United States Patent

Lee

[11] Patent Number: 5,929,316
[45] Date of Patent: Jul. 27, 1999

[54] AIR HAMMER TYPE IMPACT TESTER

[75] Inventor: Han-Peng Lee, Taipei Hsien, Taiwan

[73] Assignee: King Design Industrial Co., Ltd., Taipei Hsien, Taiwan

[21] Appl. No.: 08/898,522

[22] Filed: Jul. 22, 1997

[51] Int. Cl.⁶ ............................................. G01N 3/40
[52] U.S. Cl. ............................................. 73/12.09; 73/82
[58] Field of Search ............................ 73/12.09, 12.12, 73/82

[56] References Cited

U.S. PATENT DOCUMENTS

| | | | |
|---|---|---|---|
| 2,474,235 | 6/1949 | Dresser et al. | 73/12.09 X |
| 3,352,143 | 11/1967 | Bollar | 73/12.09 X |

*Primary Examiner*—Joseph L. Felber
*Attorney, Agent, or Firm*—Jacobson, Price, Holman & Stern, PLLC

[57] ABSTRACT

An air hammer type impact tester including a machine base having a pressure accumulation chamber with an air inlet, a straight tube vertically suspending in the pressure accumulation chamber, a test platform mounted on the machine base and having a replaceable buffer block adapted to support the sample to be tested, a hammer block moved in the straight tube to strike the buffer block against the test sample, an air pump operated to pump air into the pressure accumulation chamber, a diaphragm moved between the bottom end of the straight tube and the air inlet of the pressure accumulation chamber, the diaphragm being forced upwards by compressed air to close the bottom end of the straight tube when compressed air is pumped from the air pump into the pressure accumulation chamber, the diaphragm being forced downwardly away from the bottom end of the straight tube by air pressure when the inside pressure of the pressure accumulation chamber surpasses a predetermined value, permitting the inside pressure of the pressure accumulation chamber to pass into the straight tube and to force the hammer block upwardly against the buffer block, and a valve connected between the air pump and the air inlet of the pressure accumulation chamber to control the passage of the air inlet of the pressure accumulation chamber.

6 Claims, 4 Drawing Sheets

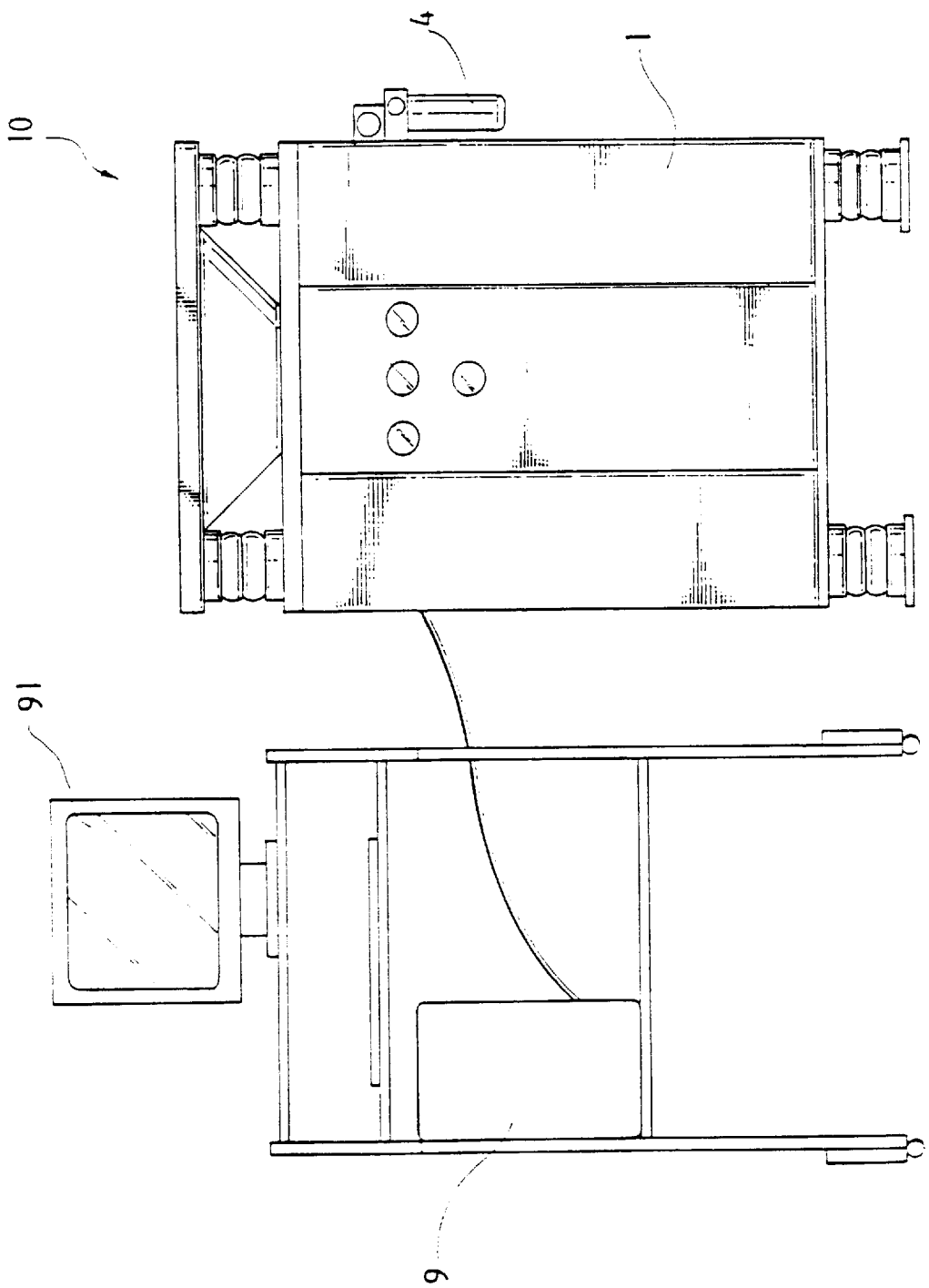

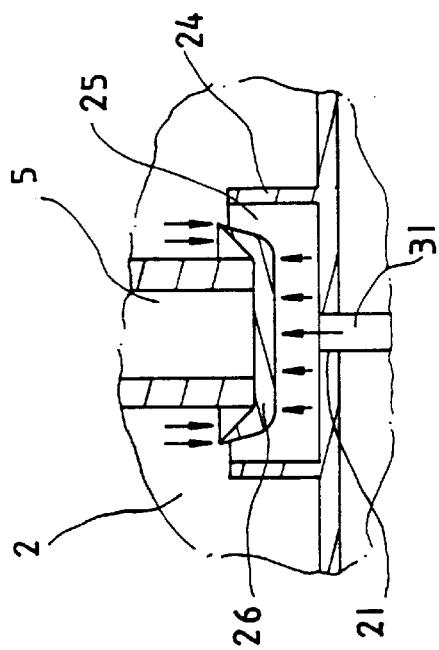
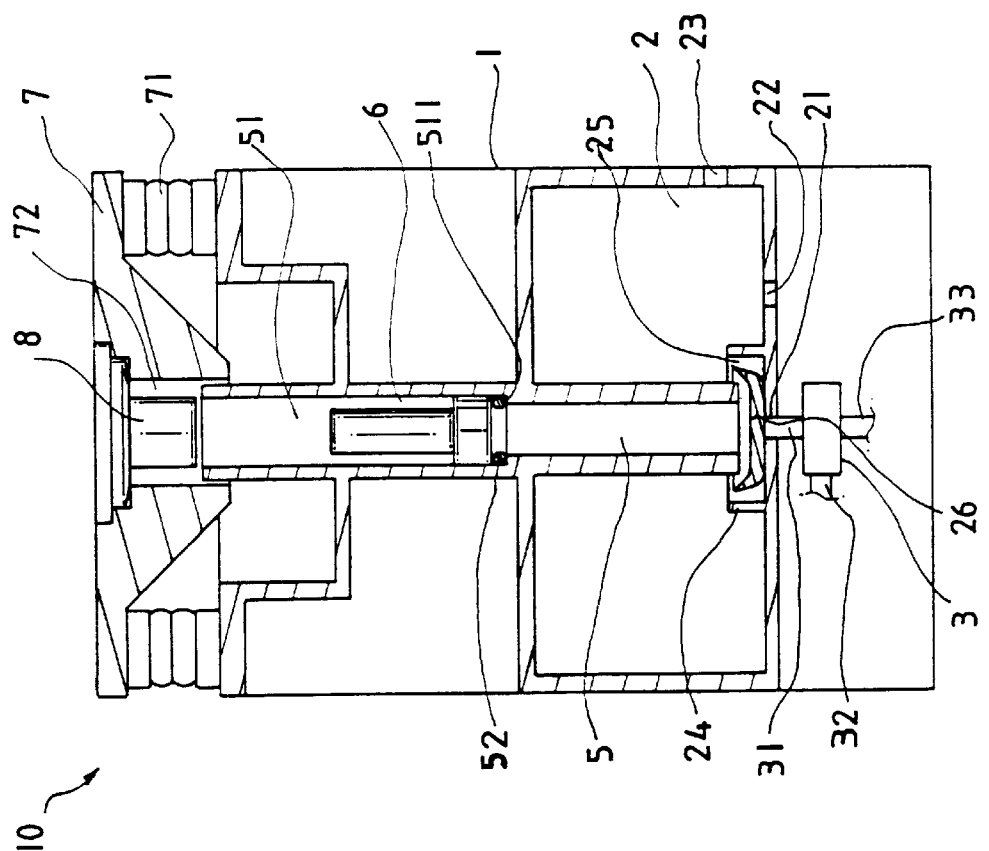

AIR HAMMER TYPE IMPACT TESTER

BACKGROUND OF THE INVENTION

The present invention relates to impact testers, and more specifically to an air hammer type impact tester which needs less installation space and, which uses air pressure to force a hammer block upwards in striking a buffer block against the test sample.

FIG. 5 shows an impact tester designed for testing the impact resistance of accessories, finished products, etc. This impact tester, referenced by 20, comprises a machine base 201, a test platform 203, two lifting mechanisms 202 controlled to lift the test platform 203. When testing a sample, the test sample is fixed to the bottom side of the test platform 203, then the test platform 203 is lifted by the lifting mechanisms 202 to a predetermined height, and then the lifting mechanisms 202 are released from the test platform 203, permitting the test platform 203 to fall down. This structure of impact tester is heavy. Because the test platform 203 must be lifted to a certain height by the lifting mechanisms 202, the height of the impact tester 20 cannot be reduced to the desired level. Therefore, this structure of impact tester is not suitable for use in any floor of a building other than the ground floor.

SUMMARY OF THE INVENTION

The present invention has been accomplished to provide an air hammer type impact tester which eliminates the aforesaid drawbacks. According to one aspect of the present invention, the air hammer type impact tester comprises a machine base having a pressure accumulation chamber with an air inlet, a straight tube vertically suspended in the pressure accumulation chamber, a test platform mounted on the machine base and having a buffer block adapted to support the sample to be tested. A hammer block is moved in the straight tube to strike the buffer block against the test sample. An air pump is operated to pump air into the pressure accumulation chamber. A diaphragm is moved between the bottom end of the straight tube and the air inlet of the pressure accumulation chamber. The diaphragm is being forced upwards by compressed air to close the bottom end of the straight tube when compressed air is pumped from the air pump into the pressure accumulation chamber. The diaphragm is forced downwardly away from the bottom end of the straight tube by air pressure when the inside pressure of the pressure accumulation chamber surpasses a predetermined value, permitting the inside pressure of the pressure accumulation chamber to pass into the straight tube and to force the hammer block upwardly against the buffer block. A valve is disposed outside the pressure accumulation chamber to control the passage of the air inlet of the pressure accumulation chamber. The valve has an air inlet connected to the air pump. A first air outlet is connected between the air inlet of the valve and the air inlet of the pressure accumulation chamber. A second air outlet is adapted for guiding compressed air away from the air inlet of the valve outside the pressure accumulation chamber when the inside pressure of the pressure accumulation chamber surpasses a predetermined value. According to another aspect of the present invention, the buffer block is replaceable so that the user can change buffer blocks of different rigidness to simulate different impact conditions.

BRIEF DESCRIPTION OF THE DRAWINGS

FIG. 1 shows an air hammer type impact tester according to the present invention;

FIG. 2 is a sectional view of the machine base of the air hammer type impact tester according to the present invention;

FIG. 3 is a sectional view in an enlarged scale of a part of the pressure accumulation chamber of the machine base according to the present invention, showing the moving direction of the rigid diagram;

DETAILED DESCRIPTION OF THE PREFERRED EMBODIMENT

Figure 4:
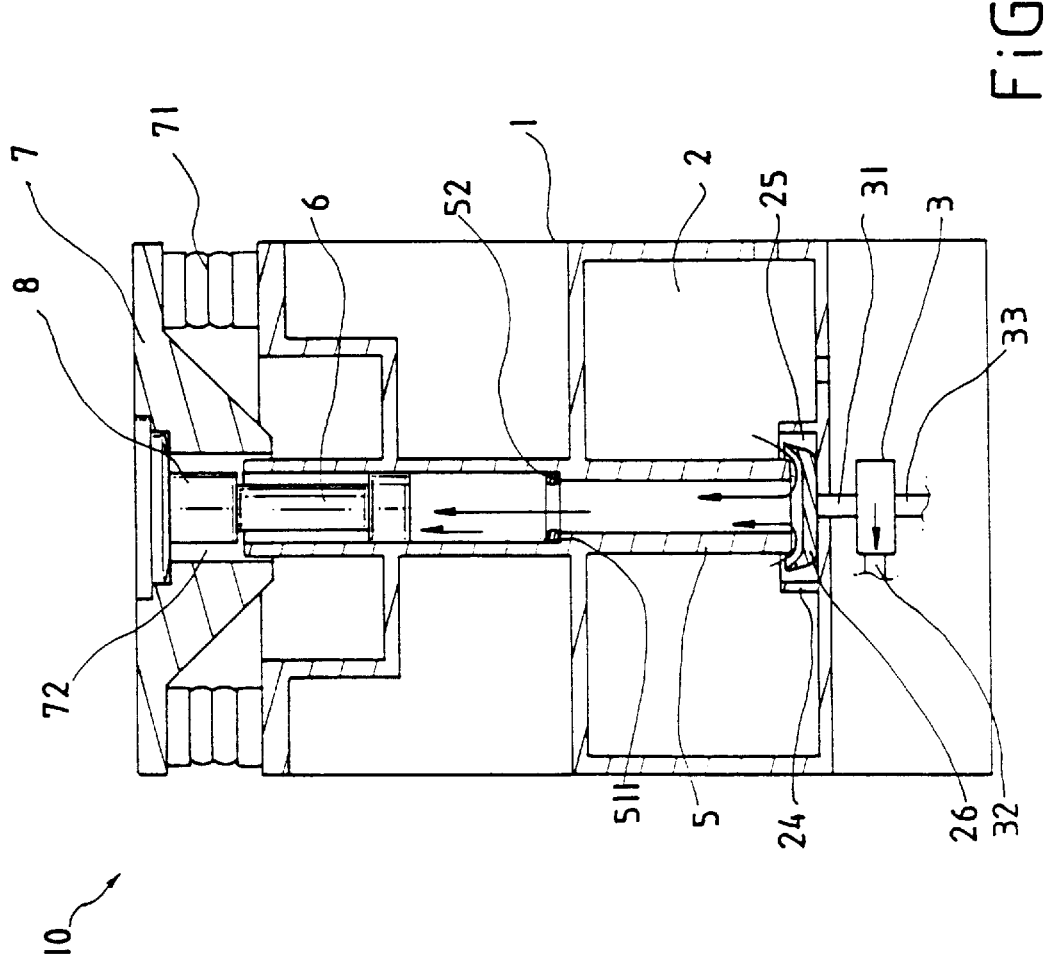
FIG. 4 is another sectional view of the machine base of the air hammer type impact tester, showing the first air outlet of the three-way valve closed, the bottom end of the straight tube opened.
Figure 5:
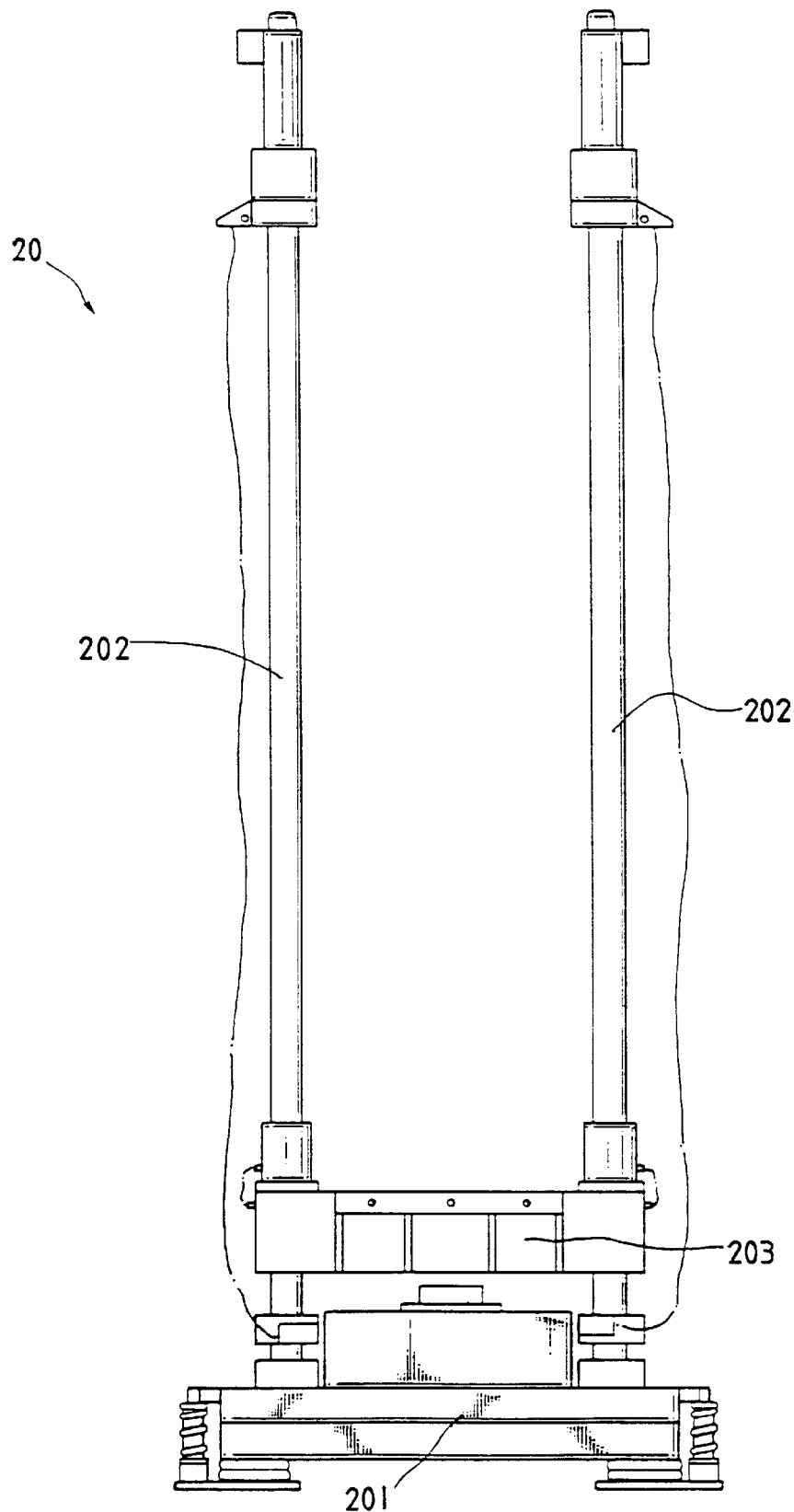
FIG. 5 shows an impact tester according to the prior art.

Referring to FIGS. 1 and 2, an air hammer type impact tester 10 in accordance with one embodiment of the present invention comprises a machine base 1. The machine base 1 comprises a pressure accumulation chamber 2, and an air inlet 21 at the bottom of the pressure accumulation chamber 2. A three-way valve 3 is provided having a first air outlet 31 connected to the air inlet 21, a second air outlet 32, and an air inlet 33 connected to an air pump 4 outside the machine base 1. The air pump 4 is operated to pump air into the pressure accumulation chamber 2 through the valve 3. The pressure accumulation chamber 2 has an exhaust (safety value) hole 22 for the exhaust of residual air pressure, and a peep hole 23 through which the condition of the inside pressure of the pressure accumulation chamber 2 is viewed. A tubular inside flange 24 is raised from the bottom wall of the pressure accumulation chamber 2 around the air inlet 21, defining a space 25 within the pressure accumulation chamber 2. A rigid diaphragm 26 is suspended within the space 25 corresponding to the air inlet 21. A straight tube 5 is vertically mounted inside the machine base 1 and aimed at the center area of the rigid diaphragm 26. The straight tube 5 has an expanded upper section 51 extended to the top of the machine base 1 and fixedly connected to the frame structure of the machine base 1, and an inside annular flange 511 raised around its inside wall at the bottom of the upper section 51. A hammer block 6 is moved in the expanded upper section 51 of the straight tube 5. An annular bumper block 52 is mounted within the straight tube 5 and supported on the inside annular flange 511 to buffer the down stroke of the hammer block 6. A test platform 7 is mounted on the top side of the machine base 1 and supported on shock absorbing cushions 71, having an opening 72 at the center vertically aligned with the straight tube 5. A replaceable rubber buffer block 8 is mounted in the opening 72 of the test platform 7.

Referring to FIGS. 3 and 4, and FIGS. 1 and 2 again, when the test sample (not shown) is mounted on the test platform 7, detectors (not shown) are attached to the test sample and connected to a host computer 9, which has a monitor 91 connected thereto. When the air pump 4 is operated to pump air into the pressure accumulation chamber 2, the rigid diaphragm 26 is forced by upward flow of air into close contact with the bottom end of the straight tube 5, and therefore air is prohibited from passing to the inside of the straight tube 5 (see FIG. 3). When the inside pressure of the pressure accumulation chamber 2 reaches a predetermined value, compressed air is stopped from passing through the first air outlet 31 into the pressure accumulation chamber 2 and forced to flow out of the second air outlet 32 of the three-way valve 3, and excessive inside pressure is allowed to pass out of the pressure accumulation chamber 2 through the air inlet 21, therefore a low pressure is formed within the pressure accumulation chamber 2 around the air inlet 21. When a low pressure is formed around the air inlet 21, the rigid diaphragm 26 is forced by air pressure to move downwards from the bottom end of the straight tube 5 toward the air inlet 21, permitting air pressure to flow in a rush from the pressure accumulation chamber 2 into the straight tube 5. When air pressure flows into the straight tube 5, the hammer block 6 is pushed upwards to strike the rubber buffer block 8 against the test sample, and test data is picked up by the detectors, then analyzed by the host computer 9, and then shown through the monitor 91 in the form of an impact wave.

Because the rubber buffer block 8 is replaceable, different rubber buffer blocks of different rigidness can be alternatively used to simulate different impact conditions.

While only one embodiment of the present invention has been shown and described, it will be understood that various modifications and changes could be made thereunto without departing from the spirit and scope of the invention disclosed.

What the invention claimed is:

1. An air hammer type impact tester comprising:

a machine base, said machine base comprising a pressure accumulation chamber having a bottom side and an air inlet at its bottom side;

a straight tube fixedly mounted inside said machine base, having a bottom end spaced above the air inlet of said pressure accumulation chamber and a top end;

a hammer block moved in said straight tube;

an air pump operated to pump air into the air inlet of said pressure accumulation chamber;

a test platform mounted on said machine base and having an opening connected to the top end of said straight tube;

a replaceable buffer block mounted in the opening of said test platform for transmitting an impact force to the test sample put on said test platform;

a diaphragm disposed inside said pressure accumulation chamber and moved between the bottom end of said straight tube and the air inlet of said pressure accumulation chamber, said diaphragm being forced upwards by compressed air to close the bottom end of said straight tube and to prohibit air pressure from passing to the inside of said straight tube when compressed air is pumped from said air pump into said pressure accumulation chamber, said diaphragm being forced downwardly away from the bottom end of said straight tube by air pressure when the inside pressure of said pressure accumulation chamber surpasses a predetermined value, permitting the inside pressure of said pressure accumulation chamber to pass into said straight tube and to force said hammer block upwardly against said buffer block; and a valve disposed outside said pressure accumulation chamber, having an air inlet connected to said air pump, a first air outlet connected between the air inlet of said valve and the air inlet of said pressure accumulation chamber, and a second air outlet adapted for guiding compressed air away from the air inlet of said valve outside said pressure accumulation chamber when the inside pressure of said pressure accumulation chamber surpasses a predetermined value.

2. The air hammer type impact tester of claim 1, wherein said pressure accumulation chamber has an exhaust hole for exhaust of residual air pressure.

3. The air hammer type impact tester of claim 1, wherein said pressure accumulation chamber has a peep hole.

4. The air hammer type impact tester of claim 1, wherein said straight tube comprises an expanded upper section which receives said hammer block, an inside annular flange raised around a bottom end of said expanded upper section on the inside, and an annular bumper block mounted inside said expanded upper section and supported on said inside annular flange for buffering said hammer block when said hammer block falls down.

5. The air hammer type impact tester of claim 1 further comprising shock absorbing cushion means mounted on said machine base and adapted to support said test platform.

6. The air hammer type impact tester of claim 1, wherein said buffer block is made of rubber.

\* \* \* \* \*